(12) United States Patent  (10) Patent No.: US 6,345,619 B1
Finn  (45) Date of Patent: Feb. 12, 2002

(54) CONTROL OF THE ADMINISTRATION OF CONTINUOUS POSITIVE AIRWAY PRESSURE TREATMENT

(75) Inventor: Shane Darren Finn, New South Wales (AU)

(73) Assignee: ResMed, Limited, North Ryde (AU)

( * ) Notice: Subject to any disclaimer, the term of this patent is extended or adjusted under 35 U.S.C. 154(b) by 0 days.

(21) Appl. No.: 09/318,032

(22) Filed: May 25, 1999

(30) Foreign Application Priority Data

May 25, 1998 (AU) .............................................. PP3701

(51) Int. Cl.⁷ .......................... A61M 16/00; A62B 7/00; F16K 31/02
(52) U.S. Cl. ............................ 128/204.21; 128/204.18; 128/204.23; 128/204.26
(58) Field of Search ....................... 128/204.18, 204.21, 128/204.23, 204.26, 205.13, 205.18, 205.24, 205.25

(56) References Cited

U.S. PATENT DOCUMENTS

| | | | |
|---|---|---|---|
| 4,944,310 A | | 7/1990 | Sullivan ...................... 128/848 |
| 5,117,819 A | * | 6/1992 | Servidio et al. ....... 128/204.18 |
| 5,148,802 A | | 9/1992 | Sanders et al. ........ 128/204.18 |
| 5,199,424 A | * | 4/1993 | Sullivan et al. ........ 128/204.18 |
| 5,390,666 A | * | 2/1995 | Kimm et al. ........... 128/204.26 |
| 5,535,738 A | * | 7/1996 | Estes et al. ............. 128/204.23 |
| 5,551,419 A | * | 9/1996 | Froehlich et al. ...... 128/204.23 |
| 5,632,269 A | * | 5/1997 | Zdrojkowski .......... 128/204.23 |
| 5,794,615 A | * | 8/1998 | Estes ...................... 128/204.23 |
| 5,803,065 A | * | 9/1998 | Zdrojkowski et al. . 128/204.23 |
| 5,865,173 A | | 2/1999 | Forehlich ............... 128/204.23 |
| 6,029,664 A | * | 2/2000 | Zdrojkowski et al. . 128/204.23 |

* cited by examiner

Primary Examiner—Aaron J. Lewis
Assistant Examiner—Joseph F. Weiss
(74) Attorney, Agent, or Firm—Pillsbury Winthrop LLP (57) ABSTRACT

A CPAP treatment apparatus has a patient mask is coupled to an air delivery conduit. The air delivery conduit is coupled to an impeller and motor, collectively forming a blower arrangement for providing a positive pressure of air to the conduit. A controller receives a signal representing respiratory flow. The controller is operable to cause the blower to supply an inspiratory phase pressure and an expiratory phase pressure. The controller selectively triggers generation of a pressure intermediate of the inspiratory phase and expiratory phase pressures for a period of time as a transitional state upon the first flow threshold being crossed. The controller also selectively triggers generation of a pressure intermediate of the expiratory phase and inspiratory phase pressures for a period of time as a transitional state upon the second flow threshold being crossed.

21 Claims, 11 Drawing Sheets

CONTROL OF THE ADMINISTRATION OF CONTINUOUS POSITIVE AIRWAY PRESSURE TREATMENT

FIELD OF THE INVENTION

This invention relates to control of the provision of Continuous Positive Airway Pressure (CPAP) treatment.

BACKGROUND OF THE INVENTION

Early forms of CPAP treatment provided pressurised air or breathable gas to the entrance of a patient's airways continuously at a pressure elevated above atmospheric pressure, typically in the range 4–20 cmH$_2$O. CPAP treatment is a common ameliorative treatment for breathing disorders, including Obstructive Sleep Apnea (OSA) syndrome. In its simplest form, CPAP treatment provides a single pressure level to the patient throughout the inspiratory and expiratory phases of respiration. It is also known for the level to vary over the course of many breaths in accordance with patient need, that form being known as automatically adjusting CPAP treatment.

Another form of CPAP treatment is 'bi-level', in which a higher pressure of gas is provided to the patient during the inspiratory phase of respiration and a relatively lower pressure during the expiratory phase. Bi-level CPAP treatment requires a determination of the onset of a transition between the inspiratory and expiratory phases (the "I-E" and "EI" transitions). The detection of these transitions is vital in controlling operation of a flow generator to provide pressurised air or breathable gas to the patient to maintain the therapeutic effect of treatment. Bi-level CPAP is used to treat respiratory insufficiency and acute respiratory failure, for example.

Many known bi-level CPAP devices rely on the detection of a change in patient respiratory flow as a trigger for a transition between treatment pressures. Delays in sensing patient breathing patterns is known to cause an increase in the work of breathing and discomfort for the patient due to pneumatic asynchrony. Such delays can also result in the unintended occurrence of apneas when treatment should be effective.

It is an objective of the present invention to overcome or at least ameliorate one or more of the problems in the prior art.

SUMMARY OF THE INVENTION

Accordingly, the gist of the invention is to provide an intermediate treatment pressure for a period of time as a transitional state between selected changes from the inspiratory and expiratory phase pressures of CPAP treatment.

Therefore, invention discloses a CPAP flow generator comprising:

a blower for providing a supply of pressurised air or breathable gas; and a controller having control over the blower to supply an inspiratory phase pressure and an expiratory phase pressure, and operable to set a first flow threshold and a second flow threshold, the controller further sensing flow due to a patient respiration and selectively triggering generation of a pressure intermediate of the inspiratory phase and expiratory phase pressures for a period of time as a transitional state upon the first flow threshold being crossed and selectively triggering generation of a pressure intermediate of the expiratory phase and the inspiratory phase pressures for a period of time as a transitional state upon the second flow threshold being crossed.

The invention further discloses CPAP treatment apparatus, comprising:

a patient mask coupled to an air delivery conduit, in turn coupled to a blower operable to provide a positive pressure of air or breathable gas to said conduit;

a blower for providing a supply of pressurised air or breathable gas; and a controller having control over the blower to supply an inspiratory phase pressure and an expiratory phase pressure, and operable to set a first flow threshold marking transitions between the inspiratory phase pressure and the expiratory phase pressure, and to set a second flow threshold, the controller further sensing flow due to a patient respiration and selectively triggering generation of a pressure intermediate of the inspiratory phase and expiratory phase pressures for a period of time as a transitional state upon the first flow threshold being crossed and selectively triggering generation of a pressure intermediate of the expiratory phase and the inspiratory phase pressures for a period of time as a transitional state upon the second flow threshold being crossed.

The invention further discloses a method for the administration of CPAP treatment, comprising the steps of:

providing a source of pressured air or breathable gas to a patient;

controlling the pressure of gas between an inspiratory phase level and a lower expiratory phase level;

setting a first patient respiratory flow threshold;

setting a second patient respiratory flow threshold; and selectively generating an intermediate pressure for a period of time as a transitional state upon the first flow threshold patient respiratory threshold being crossed; and selectively generating another intermediate pressure for a period of time as a transitional state upon the second patient respiratory flow threshold being crossed.

BRIEF DESCRIPTION OF THE DRAWINGS

Embodiments of the invention will now be described with reference to the accompanying drawings, in which.

DESCRIPTION OF PREFERRED EMBODIMENTS AND BEST MODE

Figure 1A:
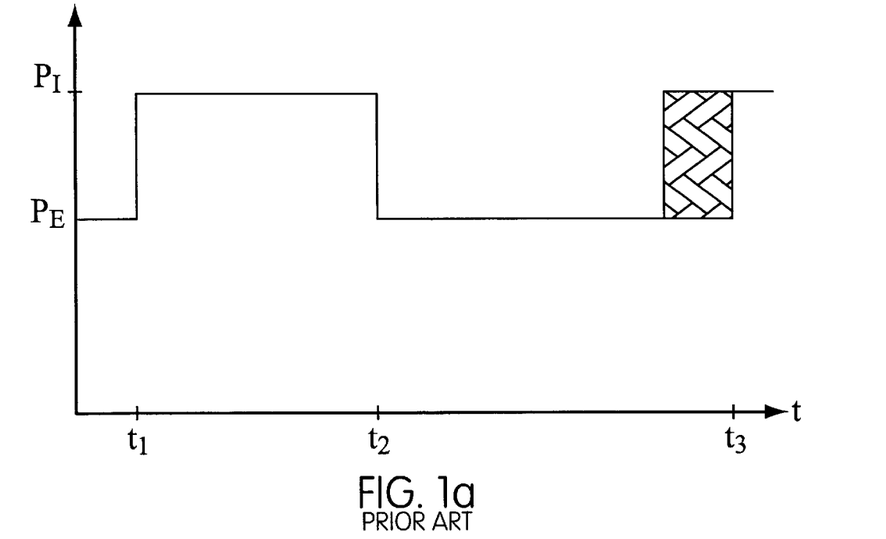
FIGS. 1*a* and 1*b* show a prior art bi-level arrangement.
Figure 1B:
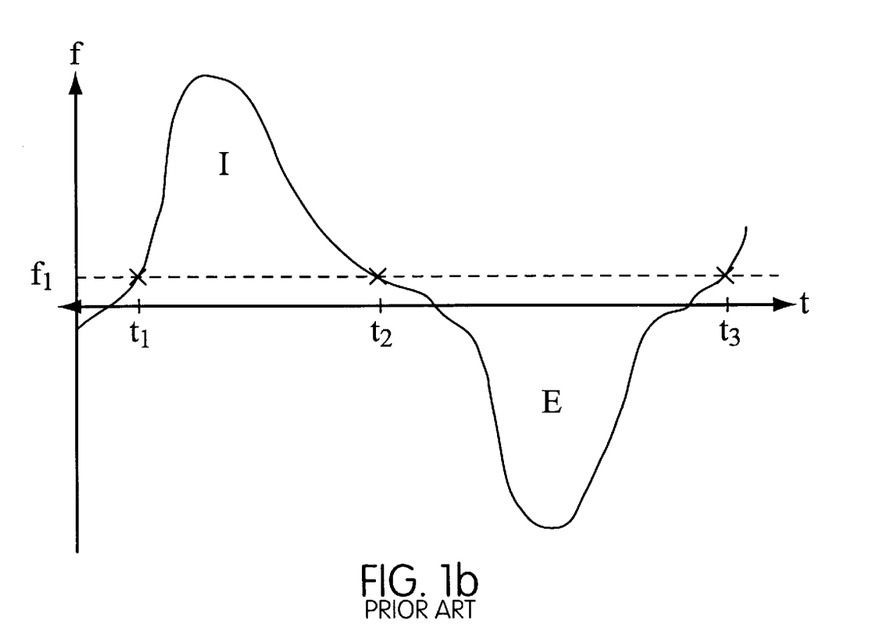

FIGS. 1*a* and 1*b* show a snapshot of slightly more than a single respiratory event, including the bi-level treatment pressures and patient respiration (flow) for the respective inspiratory (I) and expiratory (E) phases. The apparatus implementing the conventional CPAP treatment has a flow threshold, $f_1$, that is ascribed as the triggering point between inspiratory and expiratory transitions. Therefore, at time=$t_1$ it is determined that the patient has commenced inspiration and the flow generator steps the treatment pressure from the lower expiratory value $P_E$ to the high inspiratory value $P_I$. The $P_I$ level continues until time=$t_2$ when the patient flow reduces to below the threshold value $f_1$ and the lower treatment pressure $P_E$ is applied. This pressure continues until subsequent detection of the flow at time=$t_3$ increasing above the threshold $f_1$, at which time the cycle repeats.

As can be noted from the flow characteristic, high flows usually only occur during the initial portion of the respiratory phase, with the flow significantly reducing thereafter. At these low flow levels, the relatively large change in treatment pressure at the end of the inspiratory phase can cause discomfort to a patient who has, in effect, finished the work of active breathing. A further concern arises at the end of the expiratory phase (i.e. the hatched region shown in FIG. 1a), when the lower treatment pressure $P_E$ may not be adequate to prevent occlusions of the airway, and thus unintended apneas can occur.

Figure 2:
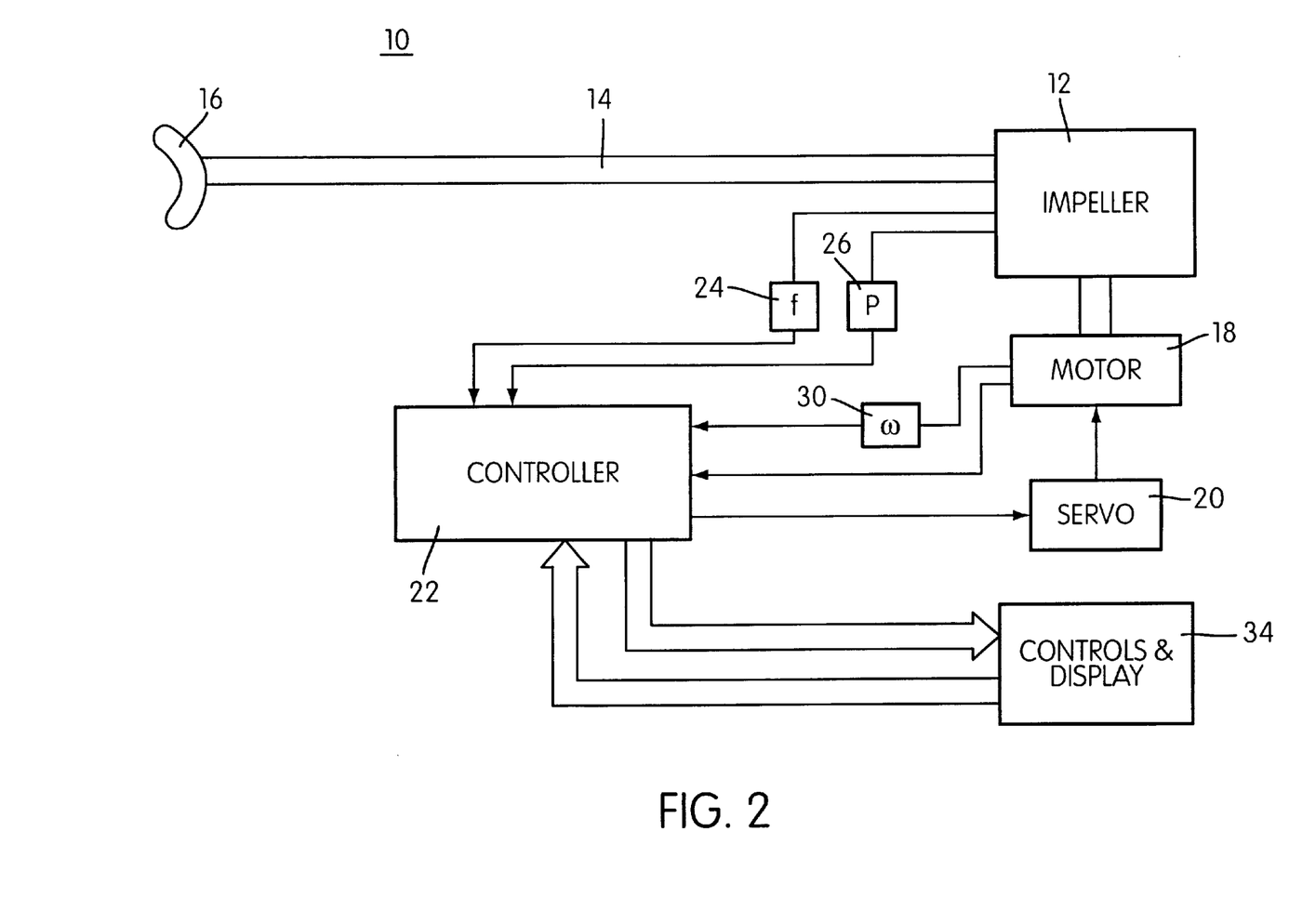
FIG. 2 shows a schematic block diagram of CPAP treatment apparatus.

FIG. 2 shows a simplified schematic block diagram of a CPAP machine 10 in which embodiments of the invention can be implemented, An impeller 12 provides air or breathable gas at a pressure elevated at above atmospheric to a flexible conduit 14, in turn coupled with a patient mask 16. The mask can be of any convenient type, and provides the air or breathable gas to the entrance of a patient's airways at the desired treatment pressure. The impeller 12 is powered by an electric motor 18, together termed a blower, under the control of a servo unit 20, to achieve the desired turbine rotational speed and thus delivery pressure applied to the conduit 14. The servo unit 20 in turn receives controlling signals from a microprocessor-based controller 22.

There are several known methods of altering the pressure delivered to the patient. In the present method, the motor speed is varied. In another method, a variable fraction of the blower outlet is diverted to atmosphere instead of being directed to the patient. In a further method, also using a single speed motor, a variable fraction of the blower inlet is choked. The invention may be embodied in devices incorporating all of these methods.

The controller 22 receives a number of input signals, including a signal representative of flow provided by a flow transducer 24 and a signal representative of delivery pressure from a pressure transducer 26. In practice one or more of these transducers may be incorporated within the controller 22, however they are shown as discrete inputs thereto for the purposes of explanation. The controller 22 also receives a signal indicative of motor speed from the motor speed sensor 30.

The controller 22 also has inputs and outputs directed to various controls and displays 34 typically located on the casing of the CPAP machine. The inputs can include push-buttons for effecting operation of the machine in a timed or spontaneous mode. The output displays can include treatment pressure indicators and 'power on' indicators.

All of the components described above are known and practised in the present applicant's Sullivan™ VPAP II machine.

Figure 3A:
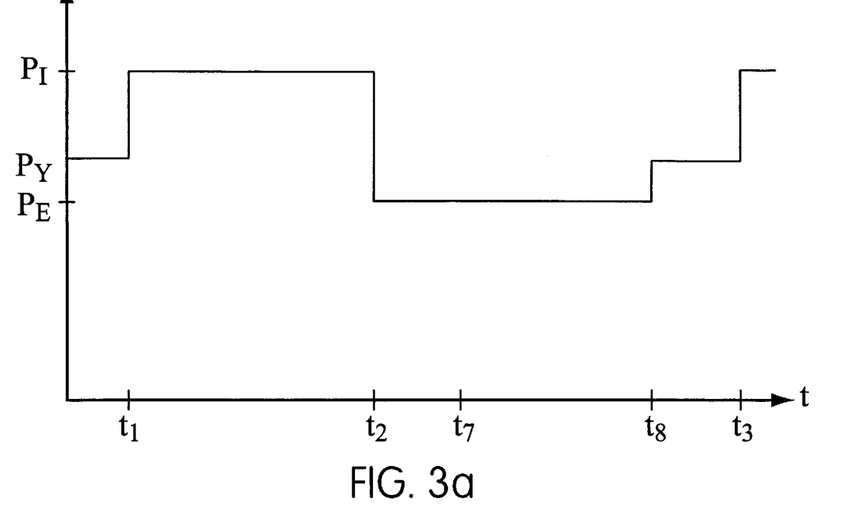
FIGS. 3*a* and 3*b* show traces of pressure and flow in one embodiment.
Figure 3B:
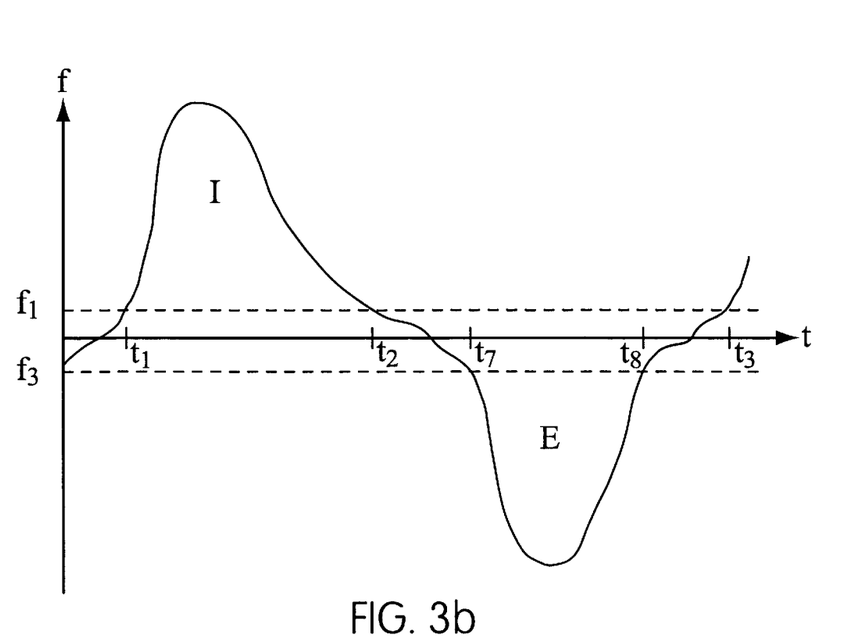

In the embodiment of FIGS. 3a and 3b a second flow threshold value, $f_3$, having a negative value, is provided. For ease of description, it is easiest to firstly consider the E-I transition. FIGS. 3a and 3b should be considered in conjunction with FIGS. 4 and 5, where the steps of the flow diagram are indicated by numerals placed in parentheses, i.e. "(50)". In the period time=$t_2$ to $t_8$, the normal expiratory pressure $P_E$ is applied (50). At time=$t_8$ the threshold $f_3$ is crossed (52) and the flow generator is caused to supply an intermediate pressure $P_Y$ (54) until time=$t_3$ (58) when the full inspiratory pressure $P_I$ is applied (60). The intermediate pressure $P_Y$ is greater than $P_E$, and, by occurring in the period between the tail end of expiration and the early stages of inspiration, the airway tends to remain splinted open, and the possibility of an apnea is reduced in the presence of time misalignment in triggering. As will be noted, whilst the flow signal passes through the threshold $f_3$ at time=$t_7$, the controller 22 is programmed to ignore this transition and maintain the lower expiratory pressure $P_E$.

It will be appreciated that the flow curve shown in FIG. 3b represents the case of no leak (e.g. no mask leak). If leak were present, then the flow curve is shifted upwards, and thus the flow thresholds $f_1$ and $f_3$ would reed to have an equivalent offset adjustment applied.

Figure 4:
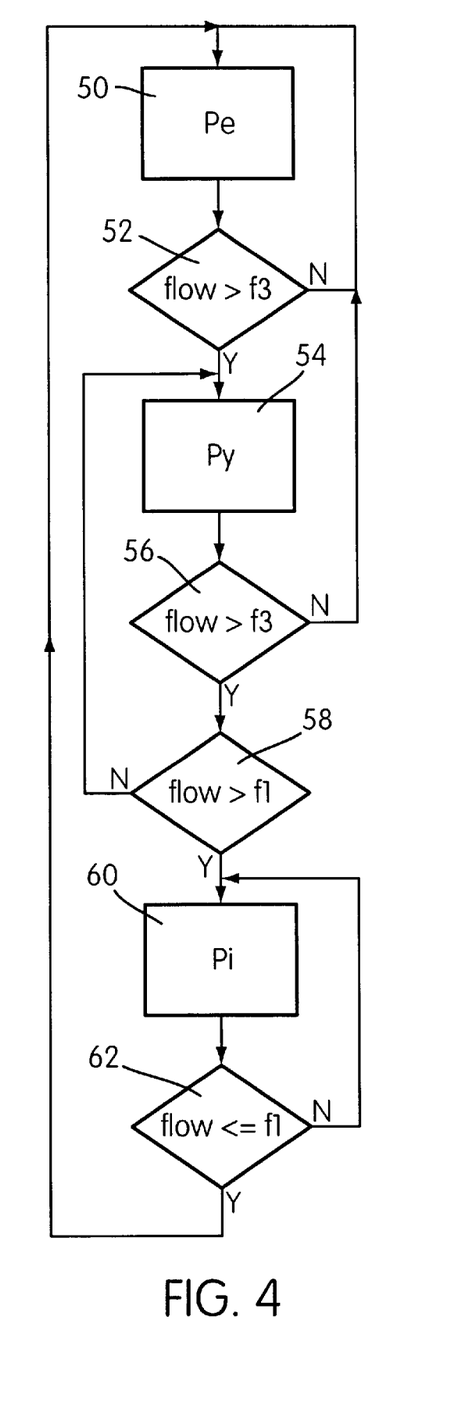
FIGS. 4 and 5 are flow diagrams relating to FIGS. 3*a* and 3*b*.
Figure 5:
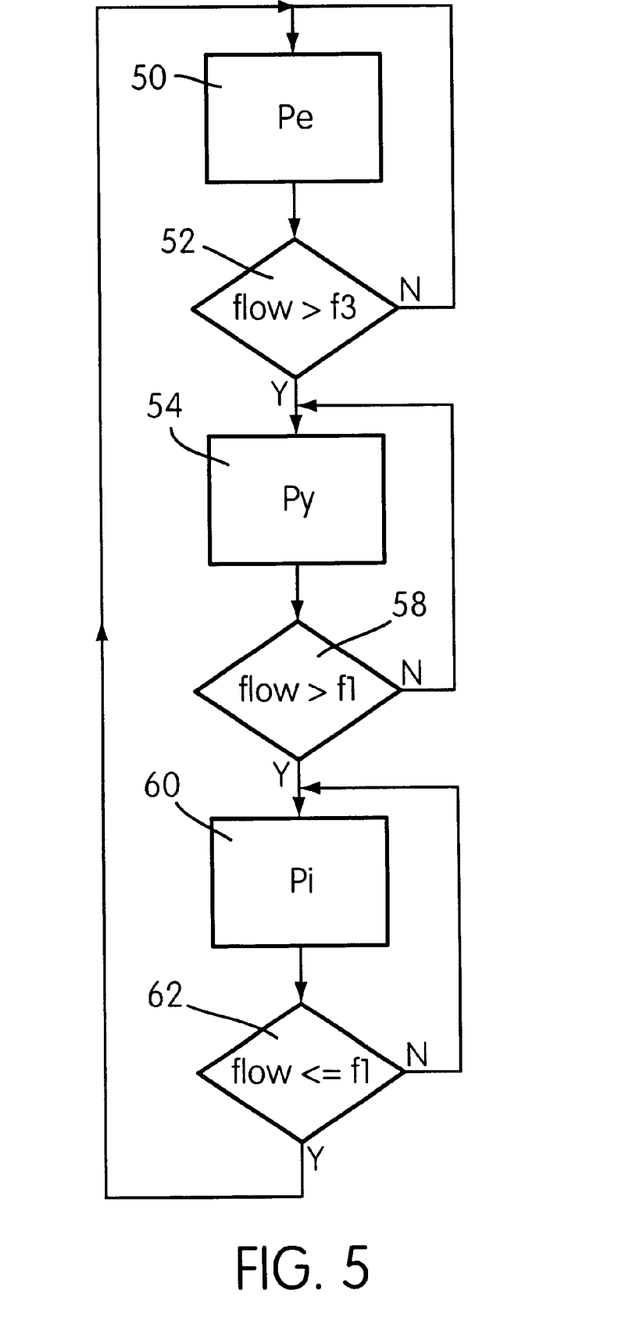

FIG. 4 has a modification over FIG. 5, in that a reversion is allowable (56) to the previous state, i.e. back to $P_E$.

Figure 6A:
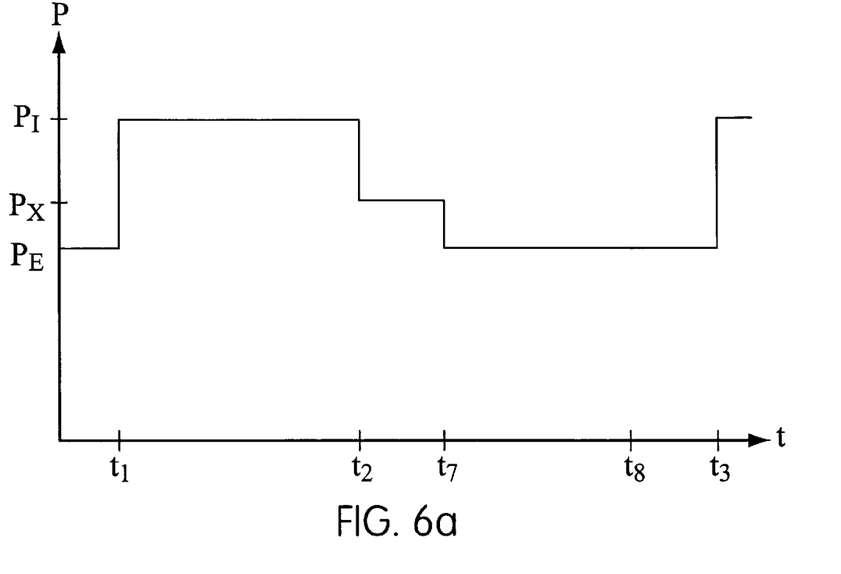
FIGS. 6*a* and 6*b* show traces of pressure and flow in another embodiment.
Figure 6B:
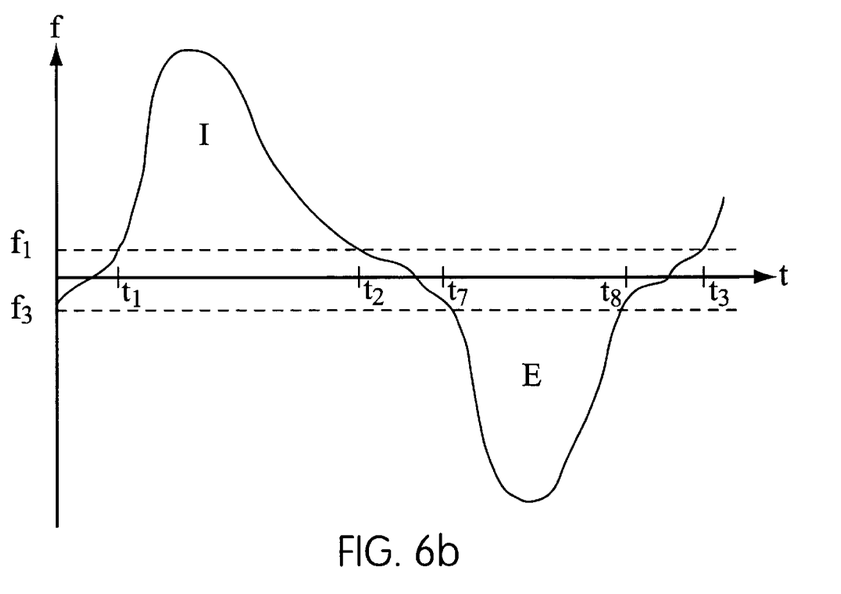
Figure 7:
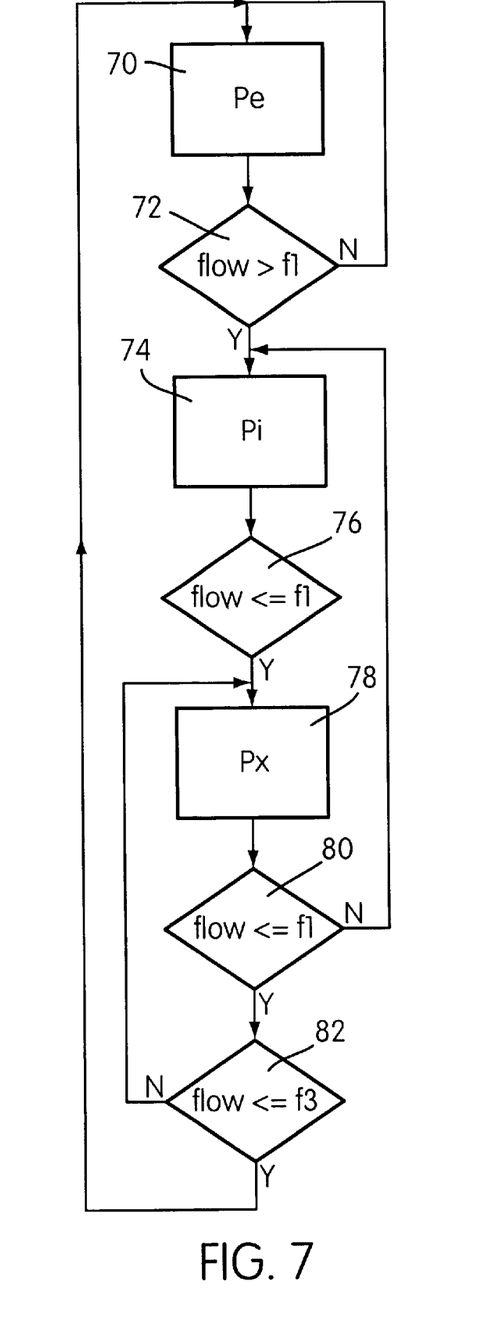
FIGS. 7 and 8 are flow diagrams relating to FIGS. 6*a* and 6*b*.
Figure 8:
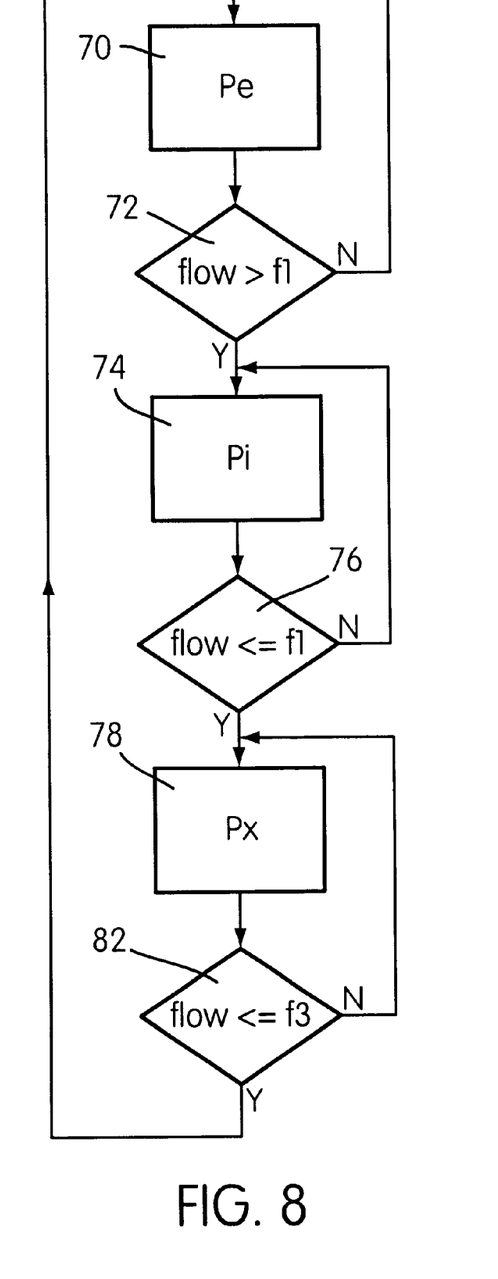

FIGS. 6a and 6b, and related flow diagrams FIGS. 7 and 8, show a further embodiment that differs from that of FIGS. 3a and 3b in that at time=$t_2$ (76) the intermediate treatment $P_X$ is applied (78) until time=$t_7$ (80,82) when the EPAP pressure $P_E$ is applied (70). This stratagem is intended to reduce the uncomfortable effect of the full pressure change between $P_I$ and $P_E$ in the low flow region between $f_1$ and $f_3$. In this embodiment, the controller 22 is programmed to ignore the flow threshold $f_3$ at time=$t_8$, waiting until the positive flow threshold $f_1$ is passed at time=$t_3$ before changing the treatment pressure from $P_E$ to $P_I$.

The flow diagram of FIG. 7 differs from FIG. 8 in that a reversion is allowable (80), i.e. back to $P_I$.

Figure 9A:
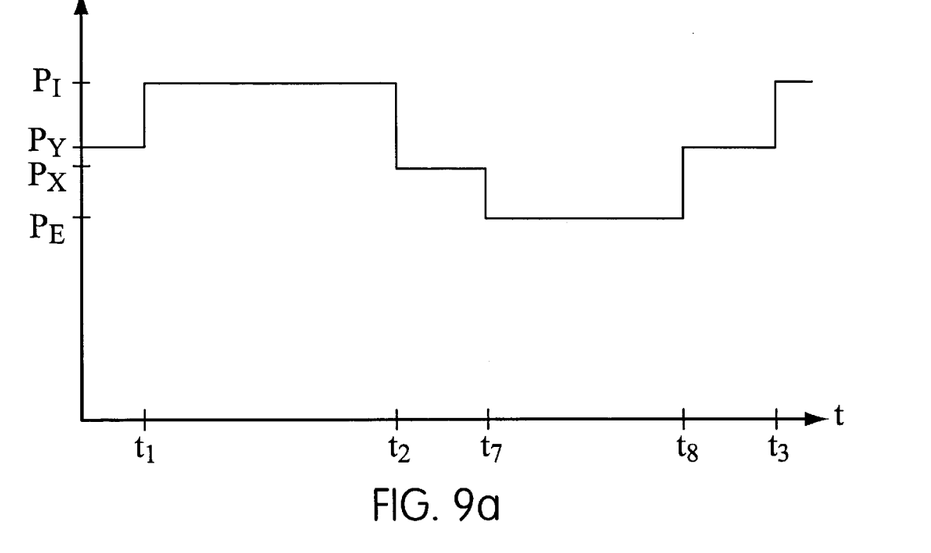
FIGS. 9*a* and 9*b* show traces of pressure and flow in yet a further embodiment.
Figure 9B:
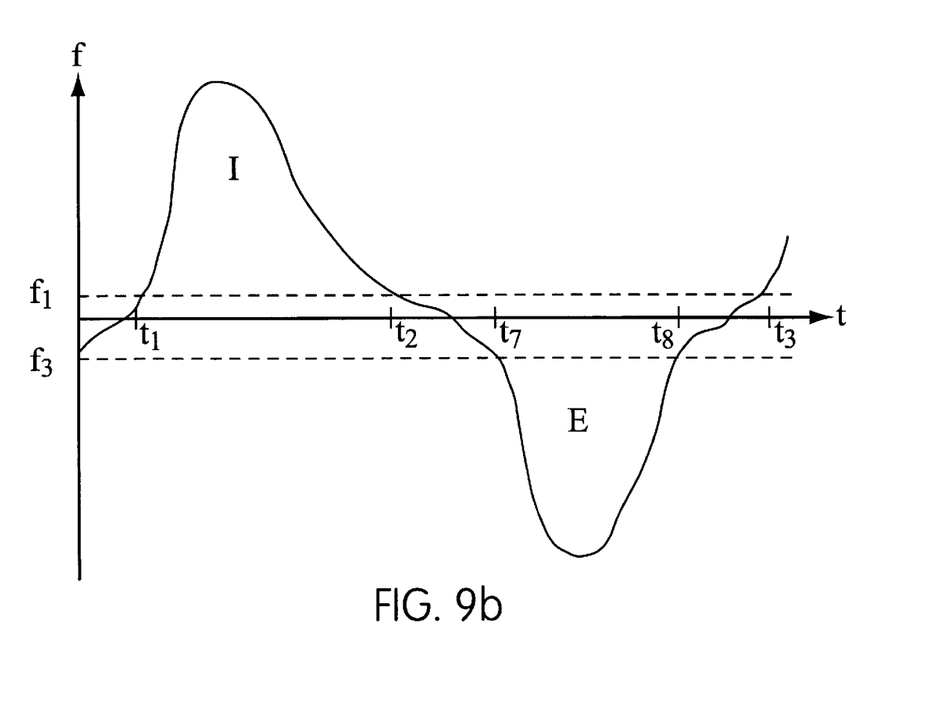
Figure 10:
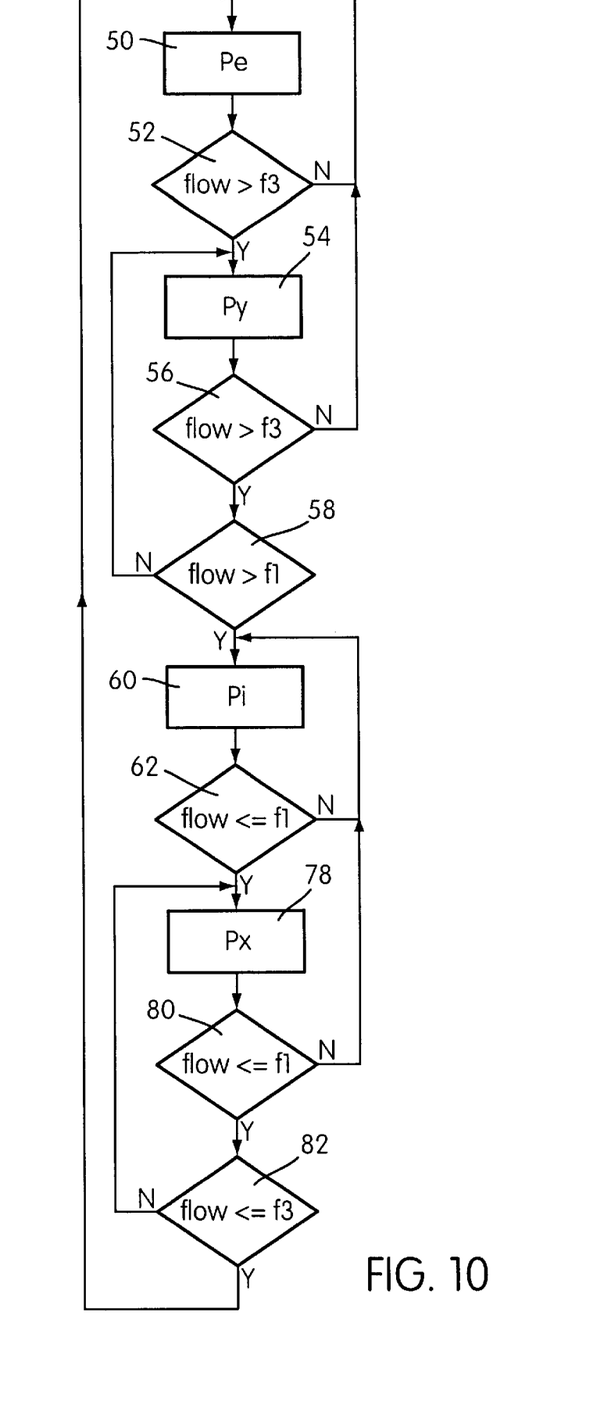
FIGS. 10 and 11 are flow diagrams relating to FIGS. 9*a* and 9*b*.
Figure 11:
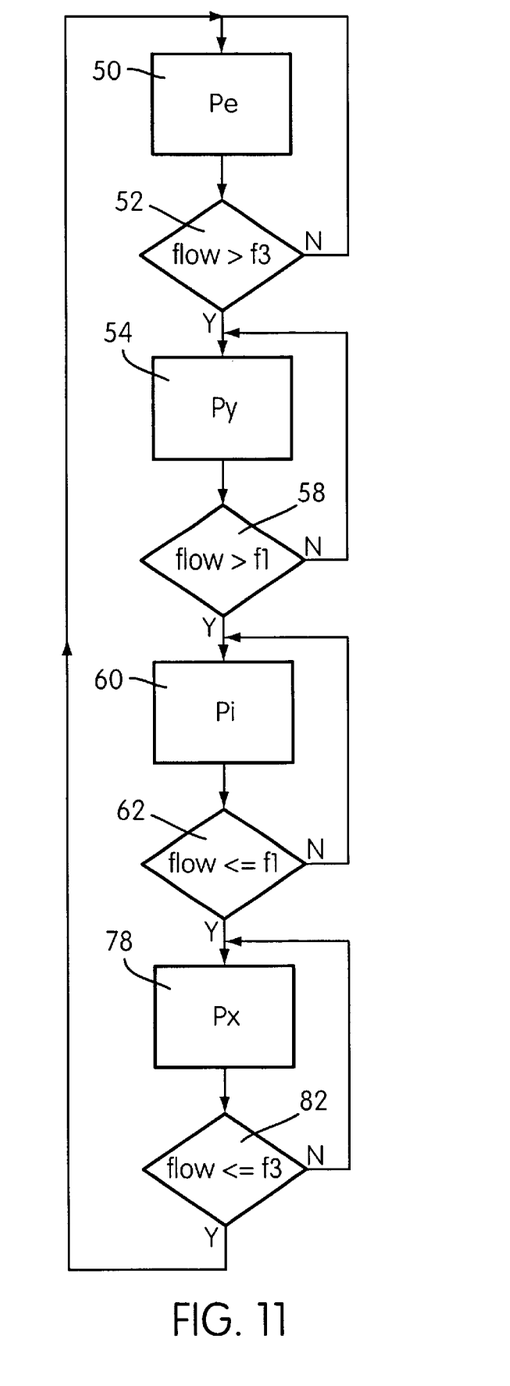

FIGS. 9a and 9b, in conjunction with FIG. 10, show a yet further embodiment that combines the intermediate pressure transitions occurring at time=$t_2$ and =$t_8$ of the previous embodiments. This embodiment thereby includes all of the benefits of the earlier embodiments. The flow diagrams of FIGS. 10 and 11 are respectively equivalent to FIGS. 4 and 5 and FIGS. 7 and 8 in combination.

In further embodiments, the pressures $P_X$ and $P_Y$ may or may not be equal.

The microcontroller 22 is appropriately programmed to give effect to the methodologies described in the preceding embodiments.

As will be apparent, numerous other arrangements are possible to derive the treatment pressure and patient respiratory flow signals that then can be that processed in the manner described above. These can include all other known forms of detection of transition between inspiration and expiration in substitution for flow per se.

Although the invention has been described with reference to preferred embodiments, it will be appreciated by those skilled in the art that the invention may be embodied in many other forms.

I claim:

1. A CPAP flow generator comprising:
    a blower for providing a supply of pressurised air or breathable gas; and
    a controller having control over the blower to supply an inspiratory phase pressure and an expiratory phase pressure, the controller being programmed to set a first flow threshold and a second flow threshold, the controller further sensing flow due to a patient respiration and at least one of 1) selectively triggering generation of a first continuous pressure at a level intermediate of the inspiratory phase and expiratory phase pressures for a period of time as a transitional state upon the first flow threshold being crossed, and 2) selectively triggering generation of a second continuous pressure at a level intermediate of the expiratory phase and the inspiratory phase pressures for a period of time as a transitional state upon the second flow threshold being crossed.

2. The CPAP flow generator as claimed in claim 1, wherein said intermediate pressure is selectively generated on the second flow threshold being crossed only during transitions from the expiratory phase pressure to the inspiratory phase pressure.

3. The CPAP flow generator as claimed in claim 1, wherein said intermediate pressure is selectively generated on the first flow threshold being crossed only during transitions from the inspiratory phase pressure to the expiratory phase pressure.

4. The CPAP flow generator as claimed in claim 1, wherein said intermediate pressure is selectively generated on the second flow threshold being crossed during transitions from the expiratory phase pressure to the inspiratory phase pressure and on the first flow threshold being crossed during transitions from the inspiratory phase pressure to the expiratory phase pressure.

5. The CPAP flow generator as claimed in claim 4, wherein the intermediate pressure is set to be at a different level depending upon whether the transition is from the inspiration phase pressure or from the expiration phase pressure.

6. The CPAP flow generator as claimed in claim 1, wherein the controller sets the intermediate pressure to be generated for a period of time falling between crossing of one of said thresholds and crossing of the next-occurring other of said thresholds.

7. The CPAP flow generator as claimed in claim 1, wherein the first flow threshold is greater than any leak flow, and the second flow threshold is less than any leak flow.

8. A CPAP treatment apparatus comprising:
   a patient mask coupled to an air delivery conduit;
   a blower for providing a supply of pressurised air or breathable gas to said patient mask via said air delivery conduit; and
   a controller having control over the blower to supply an inspiratory phase pressure and an expiratory phase pressure, and programmed to set a first flow threshold marking transitions between the inspiratory phase pressure and the expiratory phase pressure, and to set a second flow threshold, the controller further sensing flow due to a patient respiration and at least one of 1) selectively triggering generation of a continuous pressure at a level intermediate of the inspiratory phase and expiratory phase pressures for a period of time as a transitional state upon the first flow threshold being crossed, and 2) selectively triggering generation of another continuous pressure at a level intermediate of the expiratory phase and the inspiratory phase pressures for a period of time as a transitional state upon the second flow threshold being crossed.

9. The CPAP treatment apparatus as claimed in claim 8, wherein said intermediate pressure is selectively generated on the second flow threshold being crossed only during transitions from the expiratory phase pressure to the inspiratory phase pressure.

10. The CPAP treatment apparatus as claimed in claim 8, wherein said intermediate pressure is selectively generated on the first flow threshold being crossed only during transitions from the inspiratory phase pressure to the expiratory phase pressure.

11. The CPAP treatment apparatus as claimed in claim 8, wherein said intermediate pressure is selectively generated on the second flow threshold being crossed during transitions from the expiratory phase pressure to the inspiratory phase pressure and on the first flow threshold being crossed during transitions from the inspiratory phase pressure to the expiratory phase pressure.

12. The CPAP treatment apparatus as claimed in claim 11, wherein the intermediate pressure is set to be at a different level depending upon whether the transition is from the inspiration phase pressure or from the expiration phase pressure.

13. The CPAP treatment apparatus as claimed in claim 8, wherein the controller sets the intermediate pressure to be generated for a period of time falling between crossing of one of said thresholds and crossing of the next-occurring other of said thresholds.

14. The CPAP treatment apparatus as claimed in claim 8, wherein the first flow threshold is greater than any leak flow, and the second flow threshold is less than any leak flow.

15. A method for the administration of CPAP treatment comprising:
   providing a source of pressured air or breathable gas to a patient;
   controlling the pressure of the pressured air or breathable gas between an inspiratory phase level and a lower expiratory phase level;
   setting a first patient respiratory flow threshold;
   setting a second patient respiratory flow threshold; and
   at least one of 1) selectively generating a continuous intermediate pressure for a period of time as a transitional state upon the first patient respiratory flow threshold being crossed; and 2) selectively generating another continuous intermediate pressure for a period of time as a transitional state upon the second patient respiratory flow threshold being crossed.

16. A method as claimed in claim 15, whereby said intermediate pressure is selectively generated on the second flow threshold being crossed only during transitions from the expiratory phase pressure to the inspiratory phase pressure.

17. A method as claimed in claim 15, whereby said intermediate pressure is selectively generated on the first flow threshold being crossed only during transitions from the inspiratory phase pressure to the expiratory phase pressure.

18. A method as claimed in claim 15, whereby said intermediate pressure is selectively generated on the second flow threshold being crossed during transitions from the expiratory phase pressure to the inspiratory phase pressure and on the first flow threshold being crossed during transitions from the inspiratory phase pressure to the expiratory phase pressure.

19. A method as claimed in claim 18, whereby the intermediate pressure is set to be at a different level depending upon whether the transition is from the inspiration phase pressure or from the expiration phase pressure.

20. A method as claimed in claim 15, whereby the step of controlling sets the intermediate pressure to be generated for a period of time falling between crossing of one of said thresholds and crossing of the next-occurring other of said thresholds.

21. A method as claimed in claim 15, whereby the first flow threshold is greater than any leak flow, and the second flow threshold is less than any leak flow.

* * * * *